(12) United States Patent
Rubinstein et al.

(10) Patent No.: US 8,529,988 B2
(45) Date of Patent: Sep. 10, 2013

(54) METHOD FOR FABRICATION OF LOCALIZED PLASMON TRANSDUCERS

(75) Inventors: Israel Rubinstein, Rehovot (IL); Alexander Vaskevich, Rehovot (IL); Tatyana Karakouz, Rehovot (IL)

(73) Assignee: Yeda Research and Development Company Ltd., Rehovot (IL)

(*) Notice: Subject to any disclaimer, the term of this patent is extended or adjusted under 35 U.S.C. 154(b) by 342 days.

(21) Appl. No.: 12/988,067

(22) PCT Filed: Apr. 7, 2009

(86) PCT No.: PCT/IL2009/000404
§ 371 (c)(1),
(2), (4) Date: Oct. 15, 2010

(87) PCT Pub. No.: WO2009/128067
PCT Pub. Date: Oct. 22, 2009

(65) Prior Publication Data
US 2011/0033666 A1 Feb. 10, 2011

Related U.S. Application Data

(60) Provisional application No. 61/045,069, filed on Apr. 15, 2008.

(51) Int. Cl.
*C23C 16/06* (2006.01)

(52) U.S. Cl.
USPC ............... 427/123; 427/250; 427/376.3

(58) Field of Classification Search
USPC .................... 427/250, 376.3, 123
See application file for complete search history.

(56) References Cited

U.S. PATENT DOCUMENTS

| | | | |
|---|---|---|---|
| 6,342,307 B1 | 1/2002 | Menezes et al. | |
| 8,071,391 B2* | 12/2011 | Rubinstein et al. | 436/171 |
| 2006/0275541 A1* | 12/2006 | Weimer | 427/96.1 |

FOREIGN PATENT DOCUMENTS

WO 0140132 A1 6/2001

OTHER PUBLICATIONS

Royer, P., et al., "Substrate effects on surface-plasmon spectra in metal-island films". Physical Review B, vol. 35, No. 8, Mar. 15, 1987—I, pp. 3753-2762.*
Zhang, Lei, et al., "Ultrathin metal films on a metal oxide surface: Growth of Au on TiO2 (110)". Physical Review B, vol. 56, No. 16, Oct. 15, 1997—II, pp. 10 549-10 557.*
Henley, S.J., et al., "Pulsed-laser-induced nanoscale island formation in thin metal-on-oxide films". Physical Review B 72, 195408 (2005), pp. 1-10.*
Baumer, Marcus, et al., "Metal deposits on well-ordered oxide film". Progress in Surface Science 61 (1999) 127-198.*
International Search Report, mailed Jul. 28, 2010, from PCT/IL2009/000404, filed on Apr. 15, 2008.
Wanunu, M. et al, "Coordination-Based Gold Nanoparticle Layers", Journal of the American Chemical Society 2005, 127, 9207—abstract.
SPIE, POBox 10 Bellingham WA 98227-0010 USA, Jan. 1, 2008, XP040443239.
Piscopiello E. et al: "Microsopical study of Au nanocrystals self-assembled on (100)Si and SiO2/(100)Si substrates", Materials research Society Symposium Proceedingsconf—Quantum Dots: Growth, Behavior and Applications—2006 MRS Fall Meeting—Nov. 27, 2006-Dec. 1, 2006 Boston, MA, vol. 959, 2007, pp. 12-17, XP008120592.
Bittner et al., "Clusters on soft matter surfaces", Surface Science Reports, Elsevier Science, NL, vol. 61, No. 9, Nov. 1, 2006, XP025035668.
Tromp, R.M. et al. "Interdiffusion at the polyimide-Cu interface" J. Vac. Sol. Technol .A May/Jun. 1985 vol. 3, No. 3 , pp. 782-785.
Marin, N. et al,, "Diffusion of metals deposited on a polyirride film (Kapton) under and out of radiation", Nuclear Instruments and Methods in Physics Research B 105 (1995), pp. 175-180.
Hicks, E. M. et al., "Plasmonic Properties of Anchored Nanoparticles Fabricated by Reactive Ion Etching and Nanosphere Lithography" J Phys. Chem. C 2007,111. pp. 4116-4124.
Meli, M.V. et al., "Surface Plasmon Resonance of Gold Nanoparticles Arrays Partially Embedded in Quartz Substrates" , J. Phys. Chem. C 2007,111. pp. 3658-3664.

* cited by examiner

*Primary Examiner* — Bret Chen
(74) *Attorney, Agent, or Firm* — Browdy and Neimark, PLLC

(57) ABSTRACT

A method is presented for use in fabrication of metal islands on an oxide substrate. The method comprises: depositing a selected metal on the oxide substrate by evaporation of said selected metal; and annealing a film of the selected metal on said substrate at temperatures including an annealing temperature being less than 50° C. lower than a glass transition temperature, thereby forming the metal islands partially embedded in said substrate.

19 Claims, 17 Drawing Sheets

METHOD FOR FABRICATION OF LOCALIZED PLASMON TRANSDUCERS

BACKGROUND OF THE INVENTION

The invention is generally in the field of nanostructures and relates to localized plasmon transducers and methods of their fabrication, and may be used in the field of chemical and biological sensors.

Metal islands present unique optical and electronic properties, notably different from those of the bulk material. The special optical phenomena, associated with metal clusters (e.g., gold, silver, copper), may be attributed to excitation of localized surface plasmons (SPs) and observed as strong light scattering, intense light absorption, and local electromagnetic field enhancement. The localized surface plasmon resonance (LSPR) extinction band (shape, amplitude, frequency of maximum extinction) of an ensemble of Au or Ag nanoislands depends on the particle size, shape and spacing, as well as on the effective refractive index of the surrounding medium. The latter forms the basis for sensing applications based on refractive index change at the nanoisland-medium interface as a consequence of analyte binding. Optical transducers with LSPR band may be used in relatively simple and low-cost optical systems for biological and chemical sensing.

SUMMARY OF THE INVENTION

There is a need in the art for novel nanostructures for metal island films on glass and novel methods of fabrication of such films, aimed at obtaining strongly bonded and morphologically stable metal nanostructured films. This is associated with the following.

One of the effects associated with the known metal-island based LSPR transducers is the instability of such systems toward changes in the environmental conditions. This instability was experienced in experiments conducted with Ag as well as Au island films immersed in various solvents. In particular, exposure to aqueous solutions (as is a typical biological milieu) can significantly hinder the adhesion of Ag and Au island films to glass. Also, solvent immersion and drying of Au (or other noble metal) island films can cause significant changes in their morphology and optical properties. The instability can be due to (i) poor adhesion of noble metals to oxide surfaces such as glass, commonly used as a transparent substrate for LSPR measurements; (ii) high sensitivity of the optical response of metal-island based LSPR systems to small changes in the island morphology.

Generally the stability of the metal island films could be improved by relying on solvent preconditioning and avoiding drying. This technique, however, is not so widely used in applications. Somewhat more generally, the weak chemical interaction between Au and oxide substrates can be improved by using metallic (e.g. Cr, Ni, Ti) or organic (e.g. amino- or mercapto-silane; dendrimer) coupling layers. However, metal underlayers might introduce optical and chemical interference, while organic underlayers might not furnish the necessary stability.

Concerning preparation processes for Au films on various substrates, annealing or melting in the presence of oxygen can improve the bonding strength of Au to fused silica, glass, and sapphire. For example, melting of Au on silica resulted in the presence of Au in the silica near the triple gas-metal-oxide interface, as it was determined by autoradiography after removing the exposed metal by dissolution in aqua regia.

The inventors present a novel technique that can be used for obtaining strongly bonded and morphologically stable metal nanostructured (nanoisland) films on oxide substrates. Particularly, the technique of the inventors has been tested to work with a noble metal, gold (Au), directly deposited on the oxide substrate (typically a glass substrate), i.e. without any intermediate adhesion layer.

The tried deposition processes included gold thermal evaporation. The deposited Au nanostructures were annealed in the presence of oxygen at temperatures close to a glass transition temperature $T_g$ of the glass substrate. The annealing has led to (partial) embedding of Au islands in the glass substrate and stabilization of the island morphology and optical properties: upon annealing in air the Au features settled into depressions, formed in the glass and encircled by glass rims. The strong adhesion and stability of ultrasmall gold islands on glass is valuable for fundamental studies and for applications, including glass/Au optical sensing based on localized surface plasmon resonance (LSPR) spectroscopy. The islands are generally of elongated geometry (e.g. ellipsoidal-like, i.e. with aspect ratio higher than 1).

The inventors have found that deposition processes based on the metal (e.g. gold) thermal evaporation followed by annealing at temperatures close to a transition temperature of the oxide substrate resulted in the formation of a metal nanostructured film characterized by extended stability and higher refractive index sensitivity to foreign materials (chemical and biological compositions), e.g. 2-3 times higher, as compared to the conventional techniques of the kind specified.

In a broad aspect of the invention, there is provided a method of fabrication of metal islands on an oxide substrate, the method comprising:

depositing a selected metal on the oxide substrate by evaporation of said selected metal; and annealing a film of the selected metal on said substrate at temperatures including an annealing temperature being less than 50° C. lower than a transition temperature of said oxide, thereby forming the metal islands partially embedded in said substrate.

Preferably, the annealing temperature does not exceed said transition temperature of the oxide by more than 100° C.

Preferably the oxide substrate is a glass substrate. The glass may be a borosilicate glass.

The annealing temperature may be less than 20° C. lower than the glass transition temperature.

The film may be discontinuous. The annealing may take longer than 30 minutes; furthermore, it may take longer than three hours.

The annealed film may for more than 10% consist of islands of the selected metal.

As noted above, the annealed film may be in direct interaction (contact) with the substrate (glass) without any intermediate adhesive layer between the film and the glass.

In another aspect of the invention, there is provided a method of fabrication of a metal island film on glass, the method including annealing a film of a selected metal on glass in presence of oxygen, the annealing being carried out at temperatures and for a period of time selected to produce generally elongated islands partially embedded into said glass.

A majority of islands with a major axis between 5 and 400 nm may be depressed into glass for more than 0.5 nm.

In yet another aspect of the invention, there is provided a structure including a plurality of metal islands on a glass substrate, the islands being generally of an elongated geometry and being partially thermally embedded into the glass substrate.

In yet another aspect of the invention, there is provided a structure including a plurality of metal islands partially embedded into a glass substrate, a majority of the islands being embedded into depressions with a rim higher than 0.5 nm.

In yet another aspect of the invention, there is provided a structure including a plurality of metal islands partially embedded into a glass substrate, a majority of in-plane shapes of the islands having at least one crystallographic angle.

Metal islands may be applied to the substrate without an intermediate metal or organic adhesion layer. The metal may be gold (Au).

In yet another broad aspect of the invention, there is provided a method of use of the structure in solution characterization, the method including exposing the structure to a solution to be characterized without using a protective layer for the metal islands.

In yet another broad aspect of the invention, there is provided a structure including a glass substrate and a plurality of glass closed-loop nano-sized rims on the substrate, major axis of a majority of the rims being between 5 and 400 nm and heights of a majority of the rims being higher than 0.5 nm. A majority of the rims may enclose depressions with more than 0.5 nm depths, the depths being measured from main surface of the glass substrate.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In order to understand the invention and to see how it may be carried out in practice, a few embodiments of it will now be described, by way of non-limiting example only, with reference to accompanying drawings, in which.

DETAILED DESCRIPTION OF THE PREFERRED EMBODIMENTS

Details of some experiments, conducted by inventors, are herein presented. In a first series of experiments, 10 nm (nominal thickness) Au films were prepared by thermal evaporation on microscope glass cover slides (hereafter denoted cover-glass, which constitute an oxide substrate). The films were then annealed at high temperature (550-600° C.) under ambient conditions. No additional underlayers or overlayers, including intermediate adhesion layers between gold and glass, were used.

In FIGS. 1A-1D, the structure of one of such evaporated, and then annealed, film is illustrated; FIG. 1E shows a family of transmission UV-vis spectra characterizing this film.

Figure 1A:
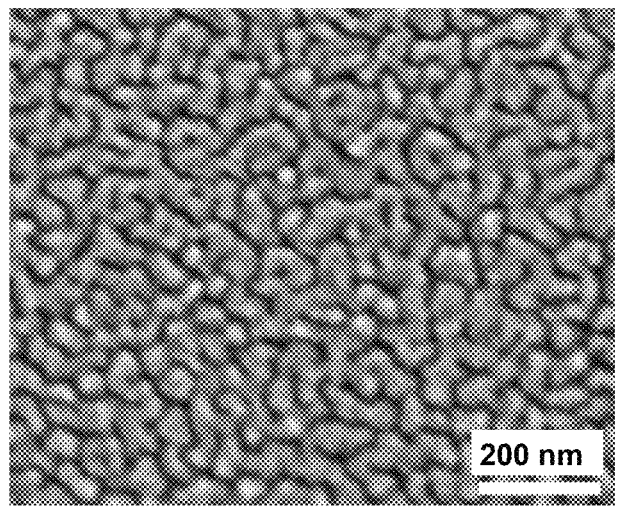
FIGS. 1A-1D are high-resolution scanning electron microscopy (SEM) images of unannealed and annealed Au island film and of an affected cover-glass substrate.
Figure 1B:
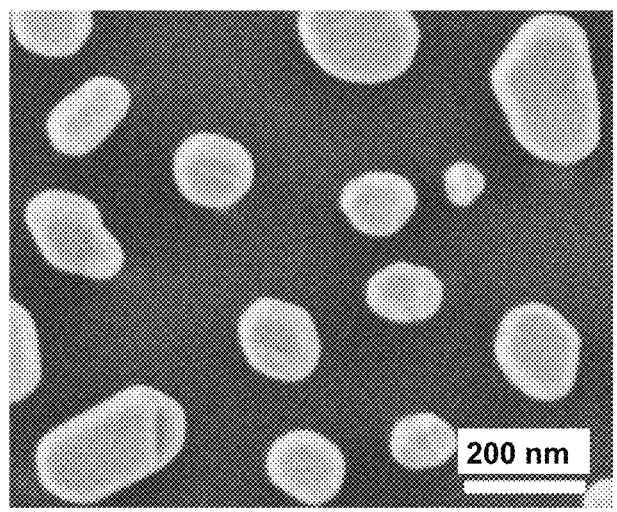
Figure 1C:
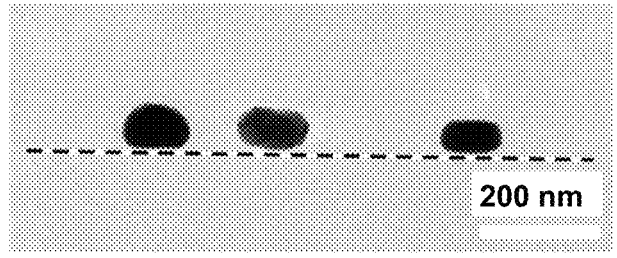
Figure 1D:
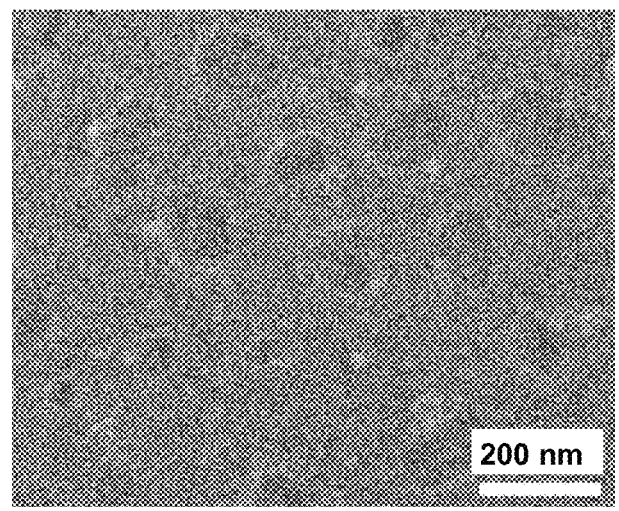
Figure 1E:
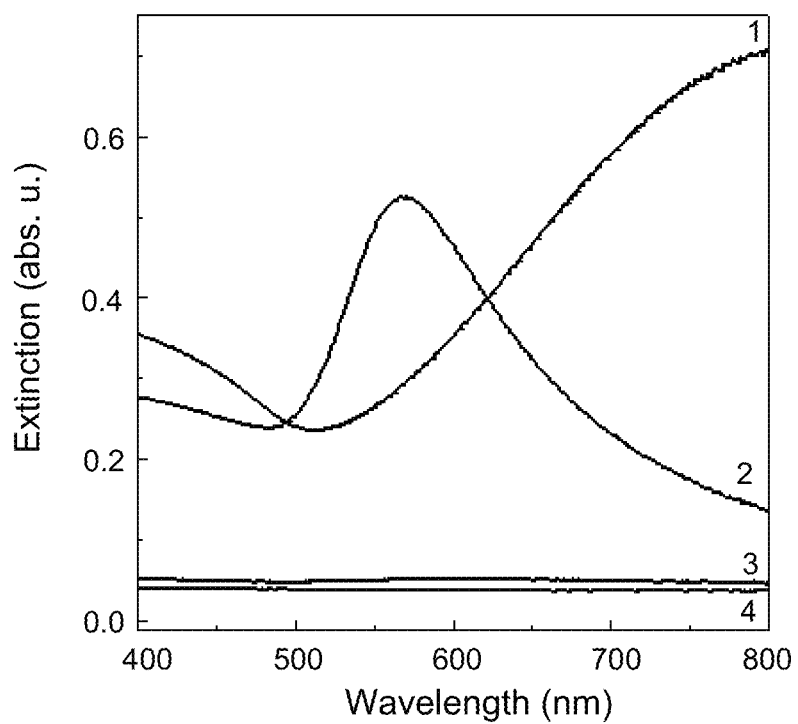
FIG. 1E is a collection of transmission UV-vis spectroscopic profiles of the unannealed and annealed Au island film and of the affected substrate.

More particularly, FIG. 1A shows a scanning electron microscopy (SEM) image of the as-evaporated film. (The scale bar drawn in the lower right corner of the image corresponds to 200 nm.) The film has a percolated structure with a network of voids: it is highly conductive. Moreover, curve 1 in FIG. 1E shows a transmission UV-vis spectrum of this film, and it is typical of continuous Au films, with an extinction minimum and the absence of the surface plasmon band.

In accordance with what was said before, the evaporated Au film was annealed for 10 hours at temperature 550° C., which is near the glass-transition temperature $T_g$ of the cover-glass substrate ($T_g$=557° C.). In FIG. 1B, there is shown a SEM image of the annealed film. It is seen that the film structure was transformed from its percolated state (FIG. 1A, before annealing) to discontinuous, thus acquiring large, well-separated, faceted islands. This major change in island morphology occurred in less than 10 min annealing. Transformation of the percolated Au film to isolated islands led to the appearance of a well-defined surface plasmon band (FIG. 1E, curve 2).

The inventors studied the sample also by cross-sectional transmission electron microscopy (TEM). The corresponding TEM image is illustrated in FIG. 1C, where the dashed line is drawn as a guide to the eye. FIG. 1C shows that the high-temperature annealed islands have elongated geometry (ellipsoidal-like or generally aspect ratio higher than 1), and also might have substantially flat top surfaces. The TEM image was obtained by the technique discussed in the article M. Wanunu, R. Popovitz-Biro, H. Cohen, A. Vaskevich, I. Rubinstein, *Journal of the American Chemical Society* 2005, 127, 9207. Such elongated metal islands resulted in high sensitivity to changes in refractive index of foreign materials that can be sensed by the structure of the present invention.

The inventors further studied how the gold deposition and annealing affected the cover-glass. To this end, they dissolved the annealed island film in aqua regia. FIG. 1D presents yet another SEM image showing the substrate modified by the deposition and annealing. As shown, there appeared island footprints. Line 3 in FIG. 1E corresponds to the transmission spectrum after Au island dissolution: this spectrum is featureless and similar to that of bare glass (line 4 in FIG. 1E).

Figure 2A:
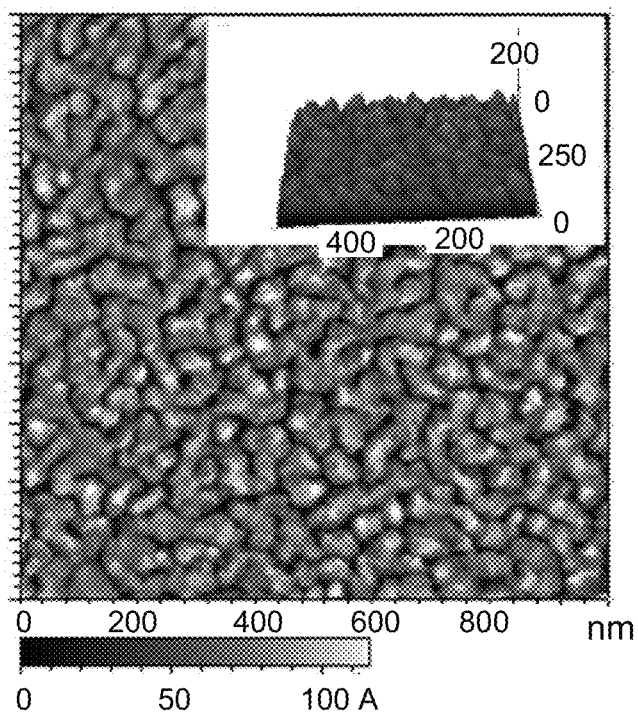
FIGS. 2A-2J are AFM images of unannealed and annealed Au island films and of the affected glass substrates.
Figure 2B:
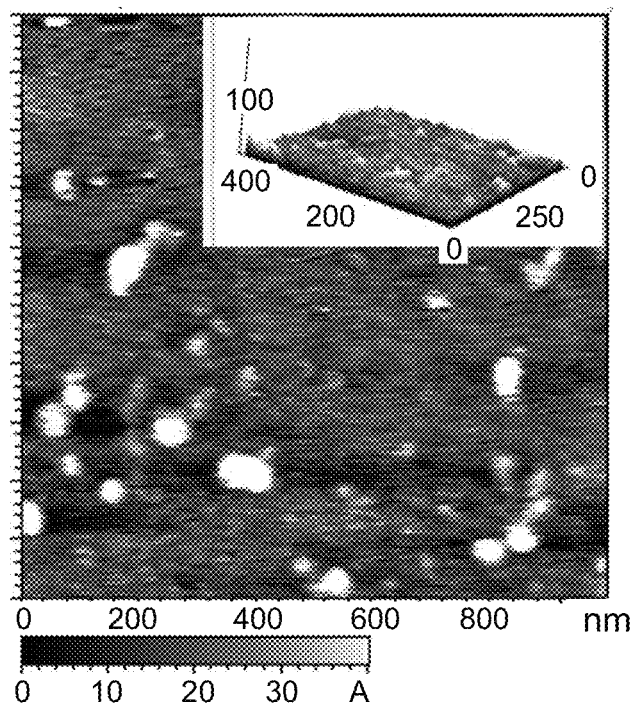
Figure 2C:
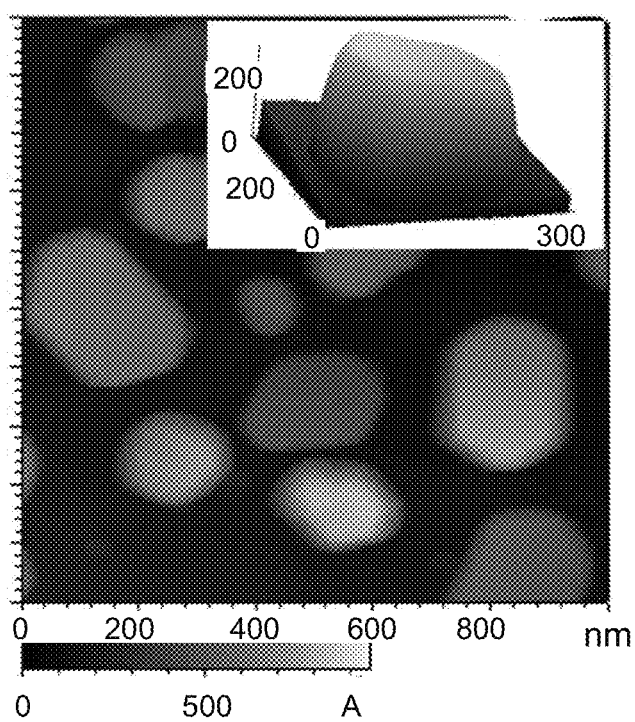
Figure 2D:
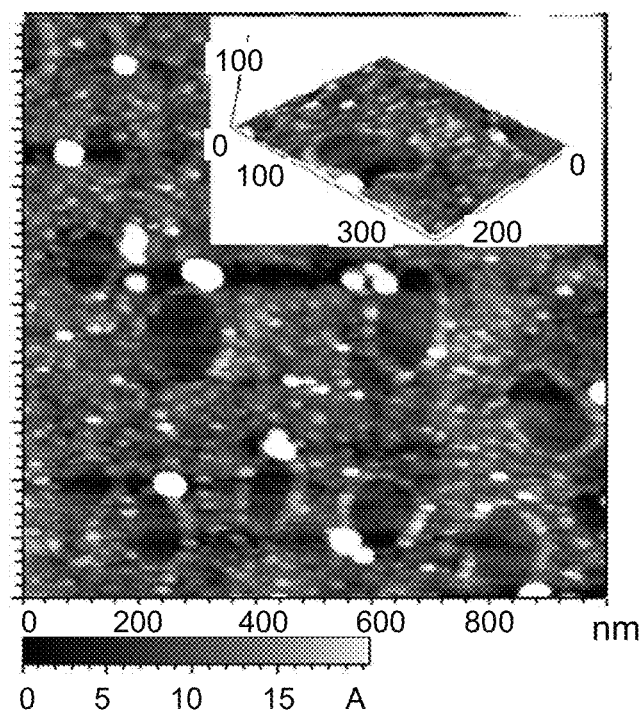
Figure 2E:
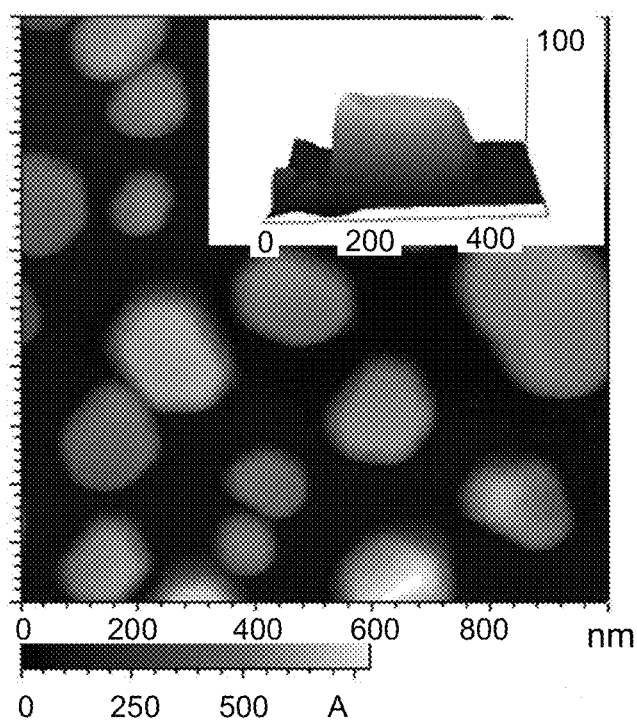
Figure 2F:
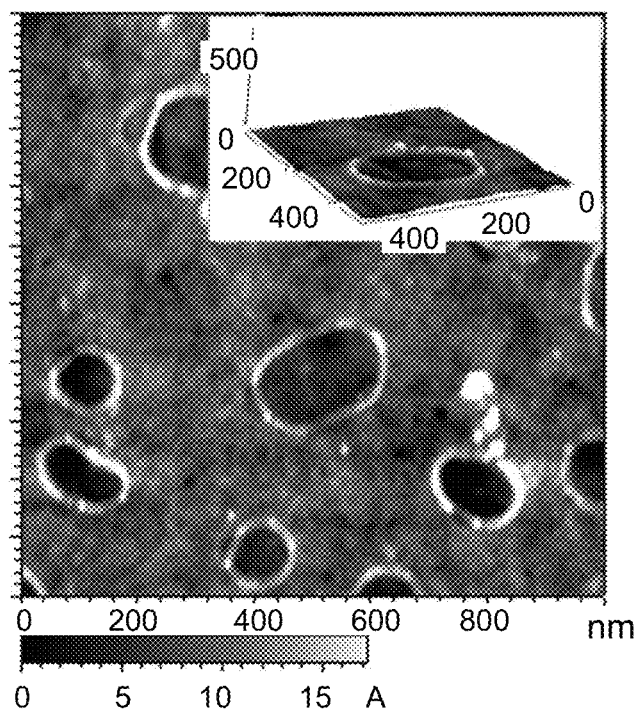
Figure 2G:
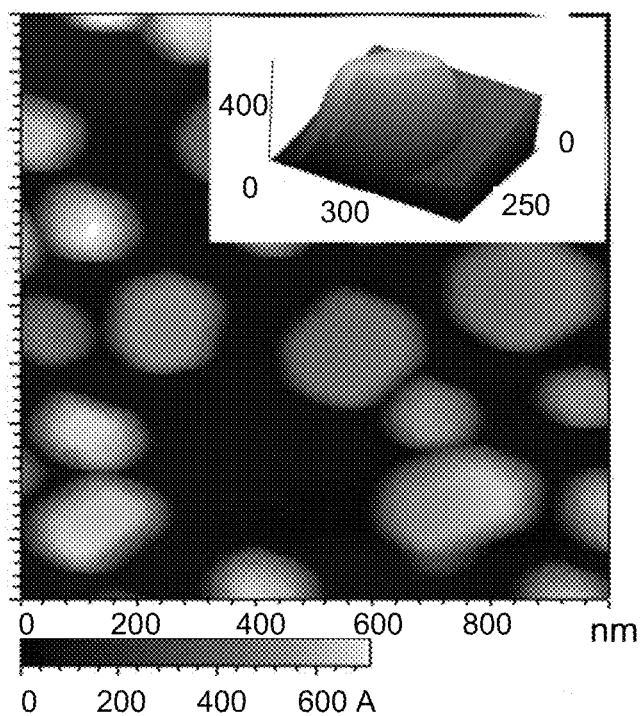
Figure 2H:
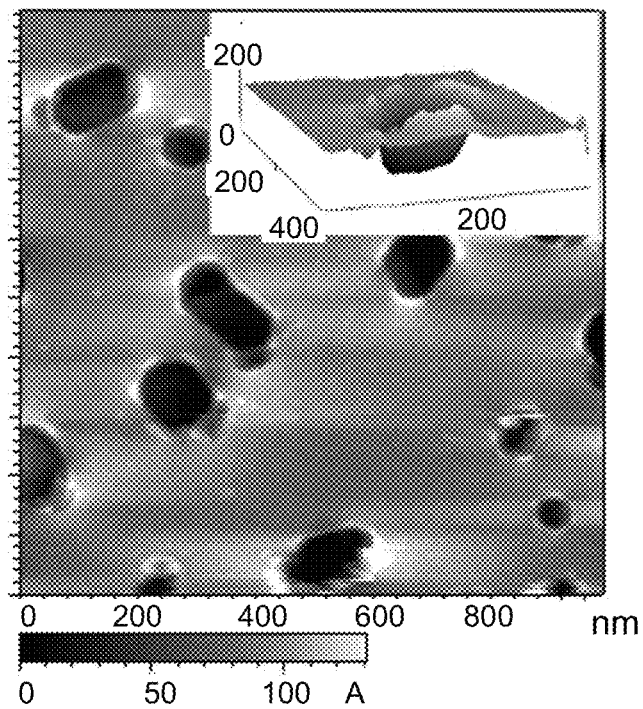
Figure 2I:
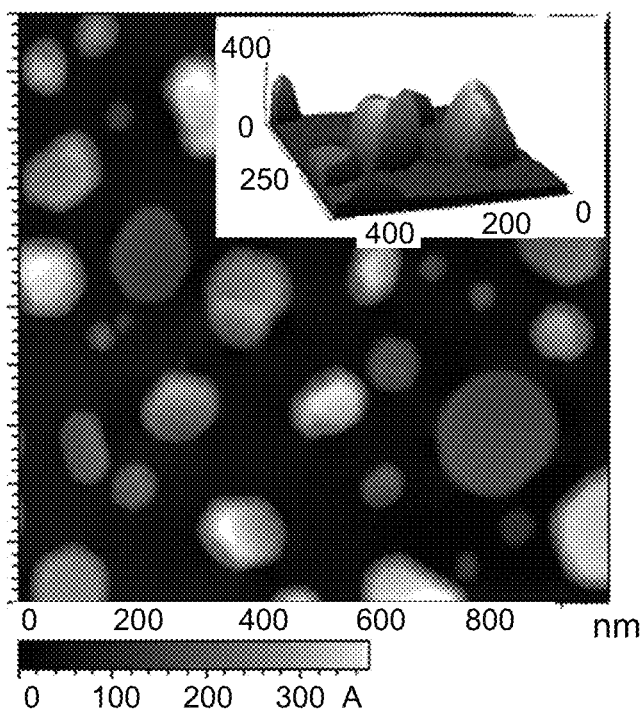
Figure 2J:
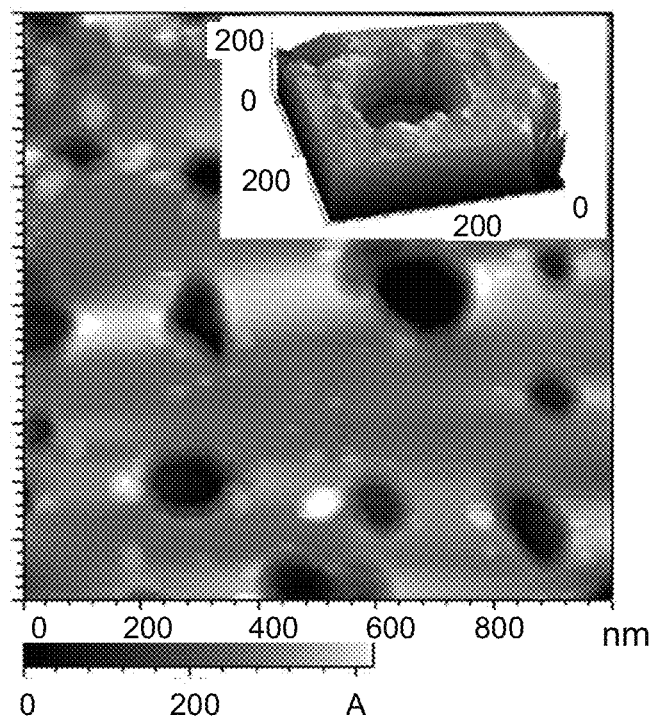

The inventors also explored the transformations of the gold island film on cover glass by atomic force microscopy (AFM). Some of the obtained AFM images are shown in FIGS. 2A-2J. Insets in these figures show 3D images of single features. Each of the illustrated AFM scans was performed over a square with one micron side, however the z-scale differs between the images. In this respect, FIGS. 2A, 2C, 2E, 2G, and 2I correspond to transducers after gold deposition and before the gold dissolution; FIGS. 2B, 2D, 2F, 2H, and 2J correspond to transducers with gold dissolved in aqua regia (i.e. to the cover-glass substrate). FIGS. 2A and 2B were obtained without the annealing step; other scans were taken after 10-hour annealing: FIGS. 2C and 2D—at temperature 500° C., FIGS. 2E and 2F—at temperature 550° C., FIGS. 2G and 2H—at temperature 600° C., and FIGS. 2I and 2J—at temperature 650° C. As it is seen, well-defined islands with large, substantially flat tops were obtained with films annealed at 500-650° C., where the top surfaces were either parallel or showed a small tilt with respect to the substrate. The AFM measured roughness of the islands' top surface was ca. 0.1 nm over 100 nm scan, indicating atomically-flat surfaces.

As commonly observed with annealed Au films, the islands' in-plane shapes typically have characteristic hexagonal angles, which is an indication of the Au {111} planes oriented parallel to the substrate surface. Accordingly, the X-ray diffraction (XRD) patterns of the annealed samples show prominent (111) and (222) peaks.

Figure 3:
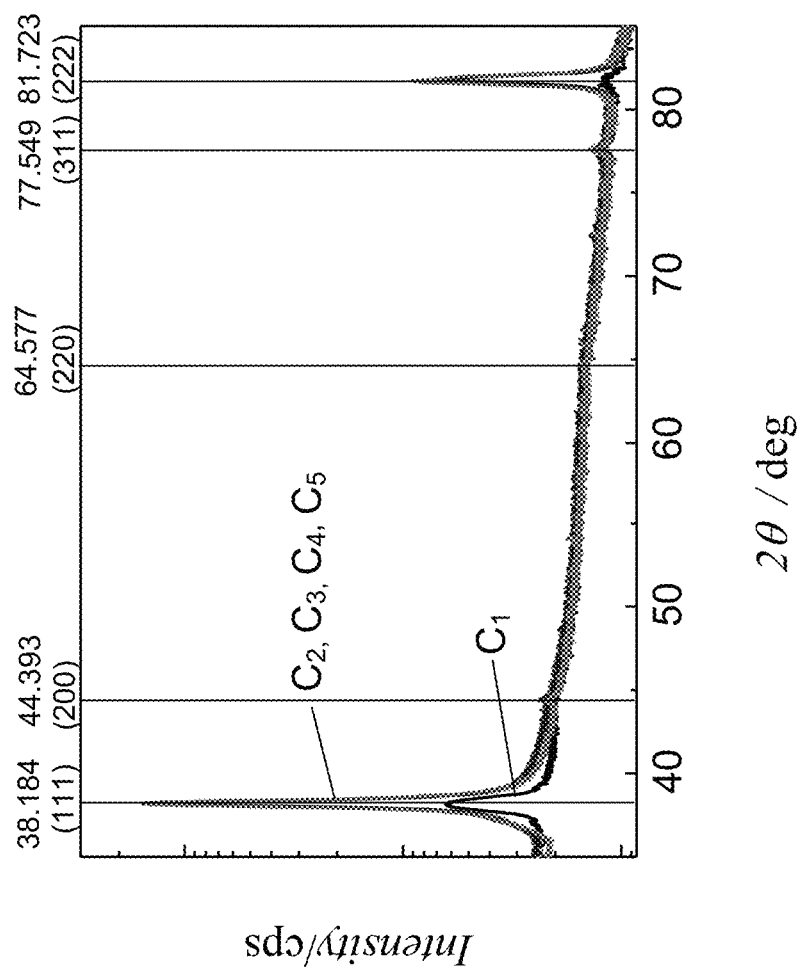
FIG. 3 is a family of X-ray diffraction (XRD) patterns for Au island films differing in temperature of annealing.
Figure 4:
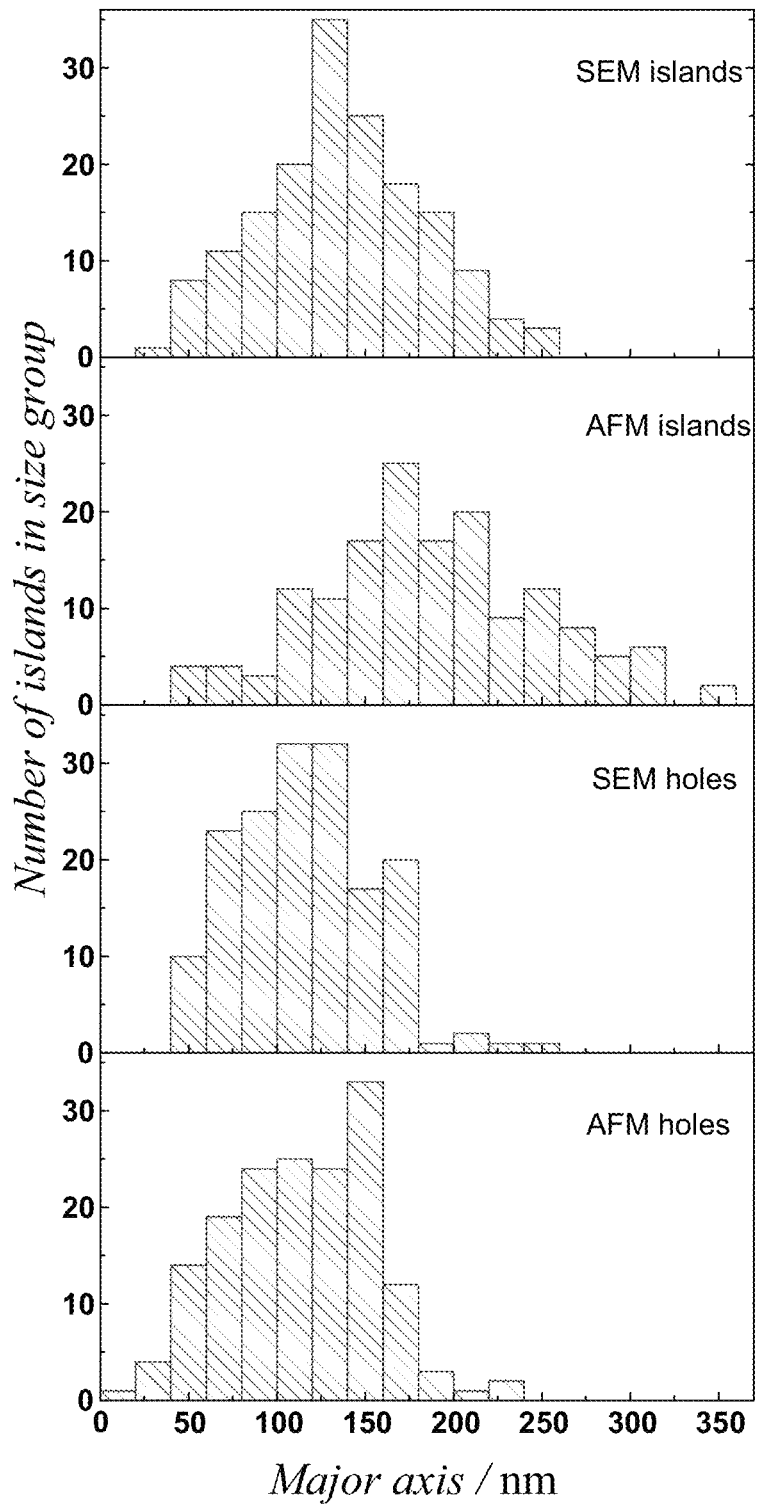
FIGS. 4A-4D are histograms of measurements of Au island heights and depression depths by methods of scanning electron microscopy and atomic force microscopy.

In FIG. 3 there are demonstrated XRD patterns obtained for an unannealed sample (curve $C_1$) and for samples annealed at temperatures 500° C., 550° C., 600° C., and 650° C. (curves $C_2$-$C_5$). It is seen that in the latter four patterns the (111) and (222) peaks are the two highest, and they are significantly higher than the same peaks in the pattern of the unannealed sample.

It should be noted, as it was mentioned above, that annealing at elevated temperatures in air resulted in drastic improvement of the adhesion between Au island films and the glass substrate. All films evaporated on cover-glass and annealed at a temperature of 550° C. or higher passed the adhesive tape test, while films annealed at lower temperatures did not.

Turning back to FIGS. 2A-2J, they are indicative of the morphology of the Au island—glass interface. AFM images of as-evaporated Au film before and after Au dissolution (FIGS. 2A and 2B) are indicative of that the flat glass surface is virtually not changed under Au evaporation without annealing. On the other hand, the AFM topography imaging (FIGS. 2D, 2F, 2H, 2J) shows actual depressions in the glass encircled by a rim. Generation of depressions and rims can also be derived from FIG. 1D. The depression depth and rim height increase with the annealing temperature.

Quantitative data on the size of the Au and glass features, obtained using AFM and SEM imaging for a film annealed at 550° C., are presented in Table 1 presenting mean values of the major axis of islands and their footprints in the cover-glass substrate for initially 10 nm Au island samples after annealing at 550° C., measured before and after Au dissolution in aqua regia.

TABLE 1

| | Method | |
|---|---|---|
| | SEM | AFM |
| Island major axis (nm) | 138 ± 46 | 185 ± 62 |
| Depression major axis (nm) | 117 ± 39 | 114 ± 42 |

The above mean values of the major axis were calculated using large statistics (150 measurements of each parameter); corresponding experimental distribution histograms are presented in FIGS. 4A-4D. More specifically, in FIGS. 4A and 4B there are presented histograms obtained from SEM and AFM measurements performed on the annealed film, and in FIGS. 4C and 4D there are presented histograms obtained from SEM and AFM measurements performed on the shallow footprints. The mean lateral dimension of the Au islands obtained by SEM is notably smaller than the value obtained from the AFM imaging. The latter is attributed to a tip convolution, which is rather severe considering the average island height after annealing of 50±15 nm (as it will be seen from Table 2 below). The mean lateral dimensions of the shallow footprints measured after island dissolution using AFM and SEM imaging are quite similar, in agreement with the much smaller depression depth (ca. 1.5 nm, again as it will be seen from Table 2) compared to the island height. The difference in the SEM-measured mean major axis of the Au islands and their footprints in the glass is attributed to the contact angle larger than 90° between the islands and the glass substrate, as seen in the cross-sectional TEM image (FIG. 1C).

In Table 2, there are presented various mean Au island heights and footprint depression depths, each calculated on the basis of respective series of fifty AFM measurements of these parameters, wherein the various series differed either in the type of glass or in the temperature of the annealing. Except the cover glass, Berliner glass, denoted high temperature glass, HTG, was used. The glass transition temperature of HTG was $T_g$=662° C., which is 105° C. higher than that of the cover-glass.

TABLE 2

| | | Annealing temperature (° C.) | | | |
|---|---|---|---|---|---|
| | | 500 | 550 | 600 | 650 |
| Island height (nm) | cover-glass | 50 ± 15 | 49 ± 15 | 41 ± 13 | 26 ± 10 |
| | HTG | | 46 ± 16 | | 51 ± 14 |
| Depression depth (nm) | cover-glass | within noise level | 1.5 ± 0.5 | 9 ± 2 | 27 ± 6 |
| | HTG | | within noise level | | 0.7 ± 0.3 |

It is seen from Table 2 and also from the above described FIGS. 2D, 2F, 2H, 2J, that the depressions in the glass became more pronounced and hole-like as the annealing temperature was raised, while more glass accumulated in the rim around the island. Accordingly, the island height (above the glass substrate) decreased.

Figure 5:
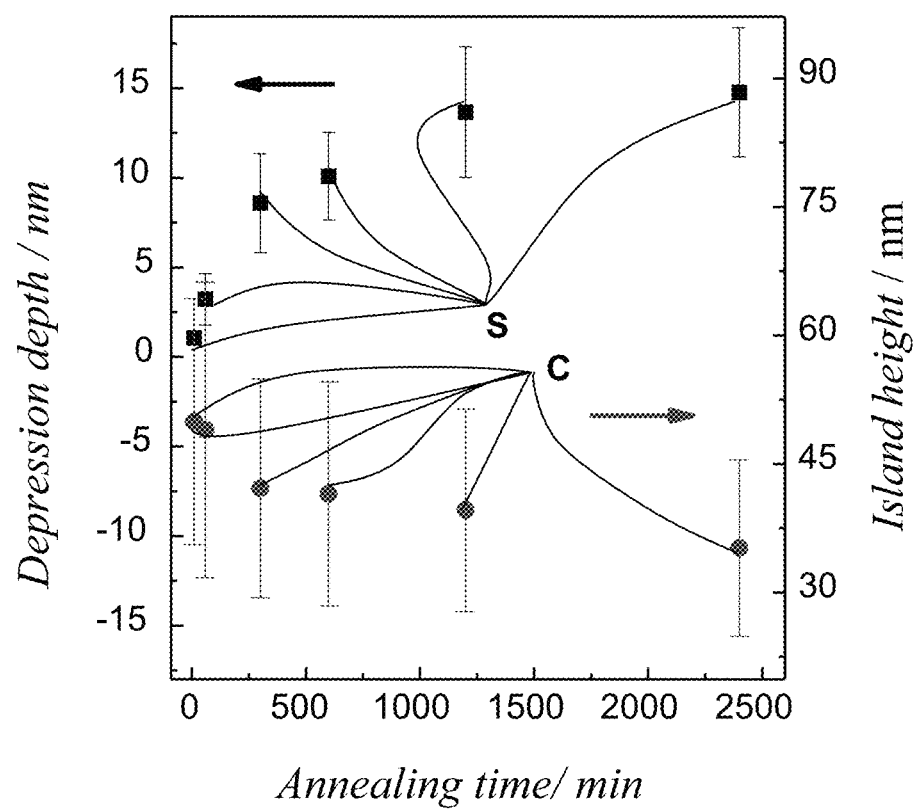
FIG. 5 is an illustration of the kinetics of island thermal embedding into glass.
Figure 6A:
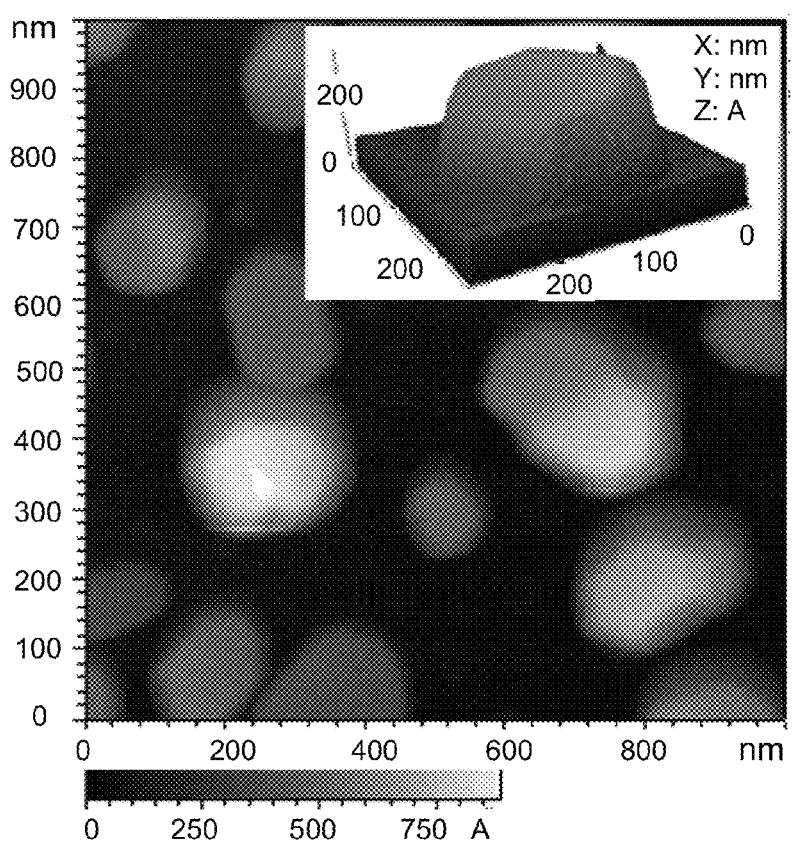
FIGS. 6A-6D are AFM images of Au island films annealed at different temperatures on Berliner glass and of the modified glass substrates.
Figure 6B:
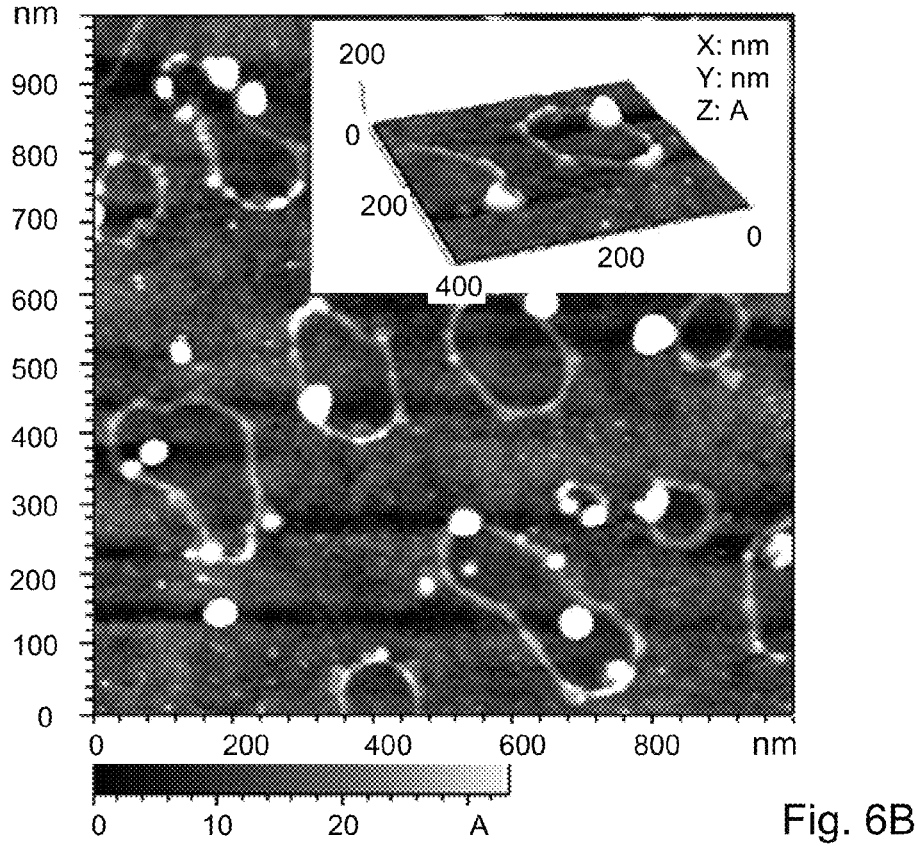
Figure 6C:
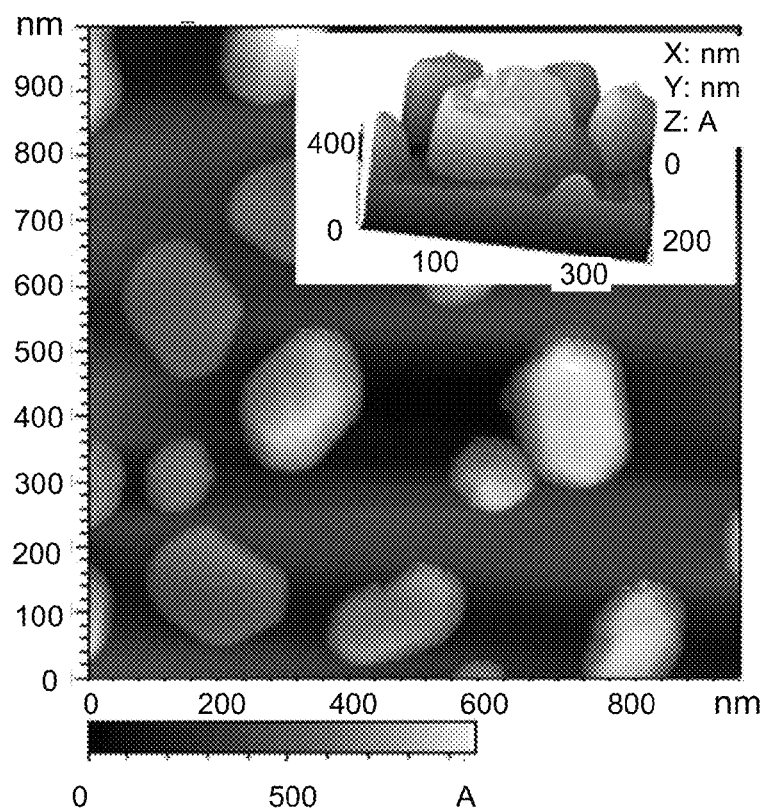
Figure 6D:
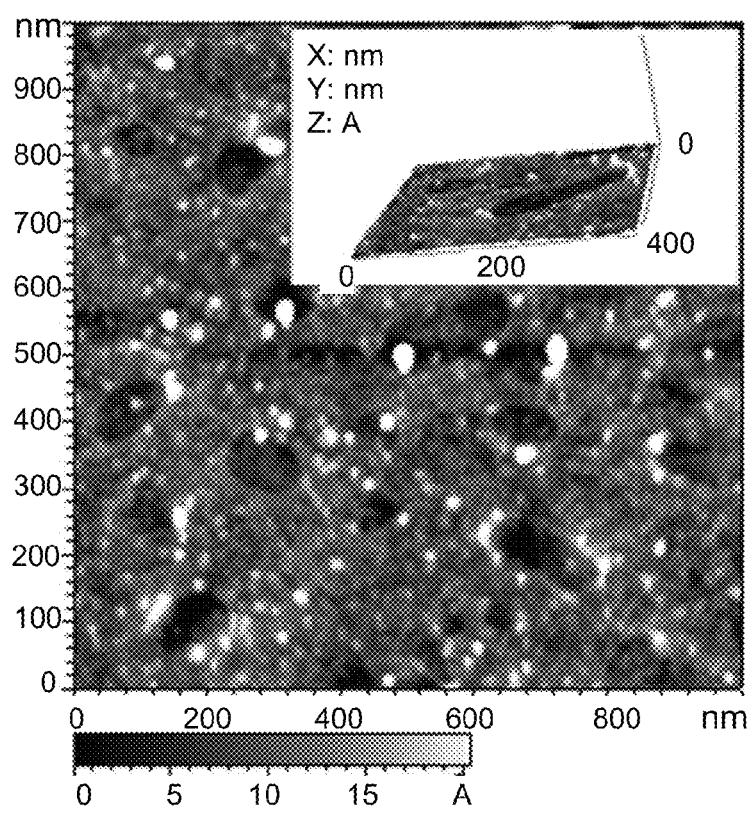

Referring to FIG. 5, it describes the kinetics of an effect of Au island embedding during annealing. In this example, annealing was applied to initially 10 nm Au island film on cover-glass and was carrier out at constant annealing temperature of 600° C. The graph shown in FIG. 5 presents the average island height above the glass substrate and the average depression depth as functions of the annealing time; average island height and the average depression depth are respectively marked with circles and squares and denoted C and S. As before, depressions were obtained by Au dissolution in aqua regia and measurements were done with the use of AFM. Each mean value was calculated from measurements of 50 islands or depressions. Standard deviations were also calculated and are shown in FIG. 5 as error bars around the mean values.

It is seen from FIG. 5 that the rate of embedding decreases with the annealing time. The sum of the mean island height and depression depth under all preparation conditions remained approximately the same at ca. 50 nm. It also should be noted, that the drastic reshaping of islands of the type caused by annealing and evident from comparison of FIG. 1A with FIG. 1B was practically complete in the first few minutes of annealing, while the embedding process, probably accompanied by subtle morphological changes in the islands, took hours. The latter phase of the fabrication process thus can be described as thermal embedding of Au islands in the glass substrate.

Turning again to the experiments with Berliner glass (HTG) (some of their results were presented in Table 2), these experiments allowed evaluating the effect of glass transition temperature $T_g$ of the glass substrate on the embedding process. In particular, in these experiments, the increase in glass transition temperature had to be accompanied by an increase in the annealing temperature. This is because the fabrication process of the stable and strongly bonded islands included the phase of thermal embedding. This said, HTG samples annealed in air for 10 h at temperatures starting from 650° C. yielded highly-stable films which passed the adhesive tape test. Except to this shift to higher annealing temperatures, obtained structures are qualitatively similar to those obtained with the cover-glass.

For example, AFM images of the annealed Au islands on HTG and of their footprints after Au dissolution shown in FIGS. 6A-6D are similar to images shown in FIGS. 2C-2J: islands tend to gradually be embedded and become surrounded by rims of glass. Here, FIGS. 6A and 6B correspond to the annealing temperature of 550° C. where no embedding is seen (see Table 2), and FIGS. 6C and 6D correspond to the annealing temperature of 650° C., where the islands are embedded (see Table 2). The as-evaporated gold film, which is not shown, was of 10 nm initial thickness. Each of the AFM scans was performed in 1×1 micron$^2$ scan field. Insets in FIGS. 6A-6D show 3D images of a single feature (i.e. island or depression). As before, the vertical (normal) scales are different for islands annealed at different temperatures.

The inventors explored the embedding mechanism with more experiments. In one experiment, they annealed Au islands on cover-glass for 10 h at 550° C. with the Au facing up in one case and facing down in another case. In both cases, the same embedding pattern was produced. In another experiment, Au island films evaporated on cover-glass were annealed at 600° C. in pure $N_2$ (inert) atmosphere. These films did not show Au island embedding, and the islands failed the adhesive tape test. The evidence on the partial thermal embedding of Au islands into glass, gathered by the inventors, is indicative of that this process occurs in the vicinity of the glass transition of the substrate, that there is no gravitational effect, and that the presence of a reactive atmosphere, such as atmosphere with oxygen, is required.

For application of Au island films as LSPR transducers not only structural stability (e.g., passing the adhesive tape test), but also stability of the optical response toward dipping in solvents and drying, is desired. However, subjecting islands to solvents and capillary forces can modify or move islands. The stability of the morphology and optical response of Au island films evaporated on cover-glass and annealed at high temperatures (embedded films) and its relevance to sensing applications, were evaluated and compared with non-embedded films. Both types of transducers were similarly subjected to a number of treatments including those common in biosensing. These include washing in ethanol and in phosphate buffer saline (PBS) solution, the latter being the most common biological solvent; self-assembly (SA) of an alkanethiol monolayer; self-assembly of a 5' thiol-modified oligonucleotide (ss-DNA, 43 bases); and protein recognition (immunoassay) using IgG proteins. (The ss-DNA was 5'-modified with a $-(CH_2)_6-S-S-(CH_2)_6-OH$ group and was used as purchased.)

Figure 7A:
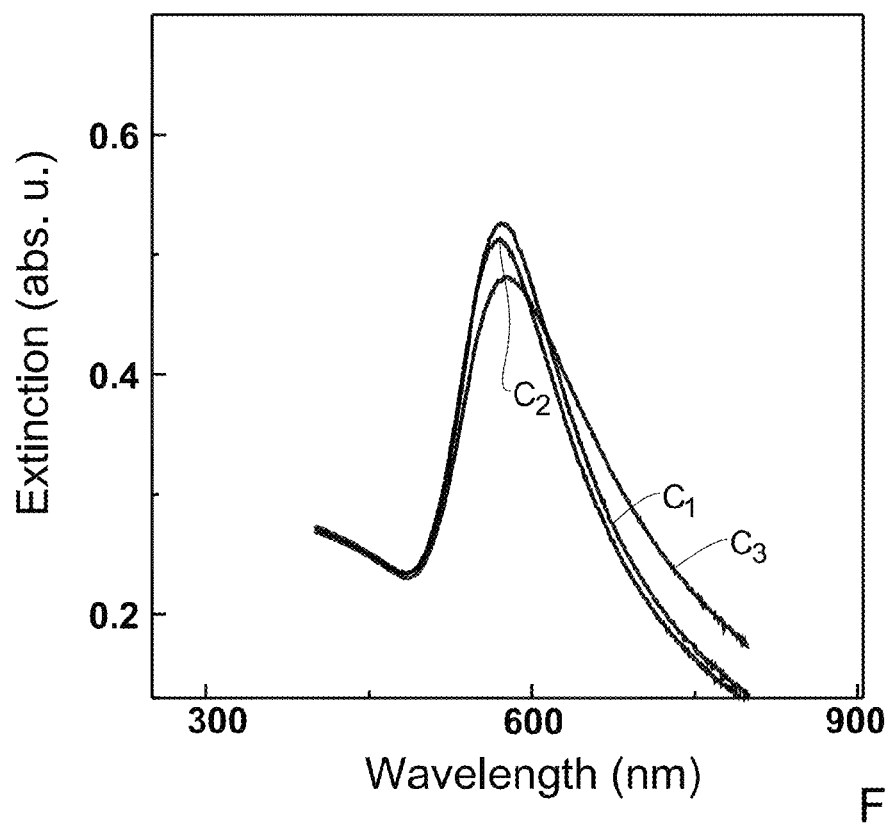
FIGS. 7A and 7B present transmission UV-vis extinction spectra of Au island films differing by annealing temperature, before and after the film is brought into contact with non-inert medium.
Figure 7B:
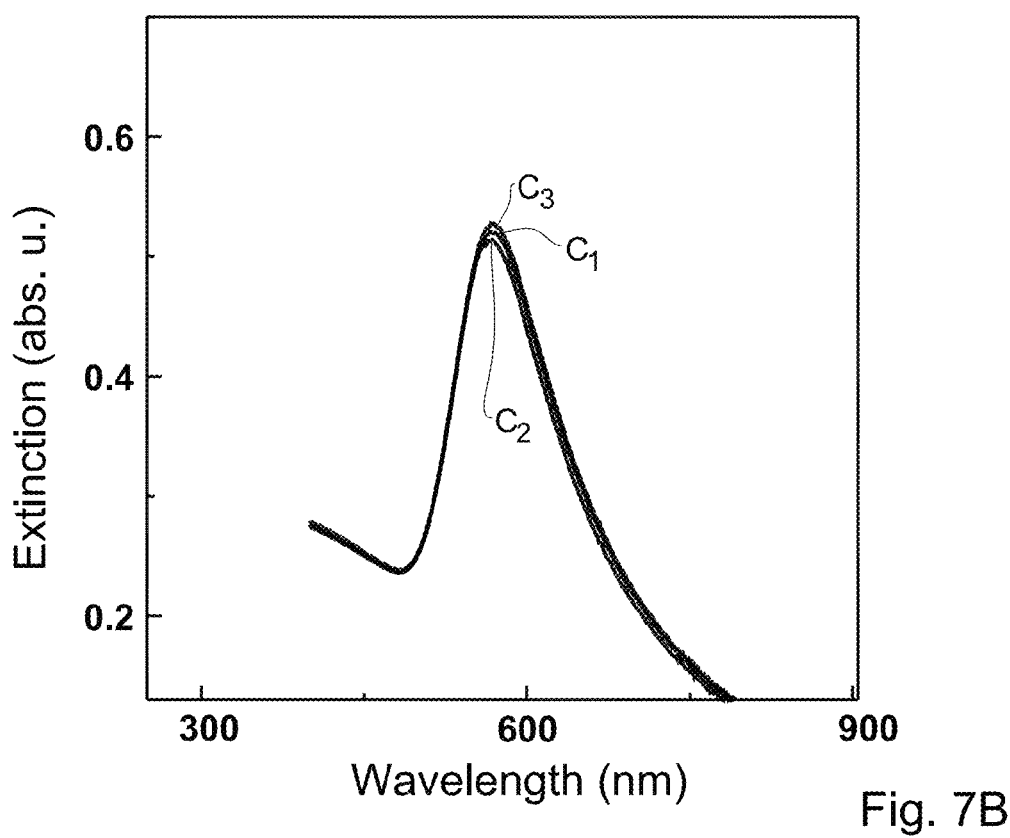
Figure 7C:
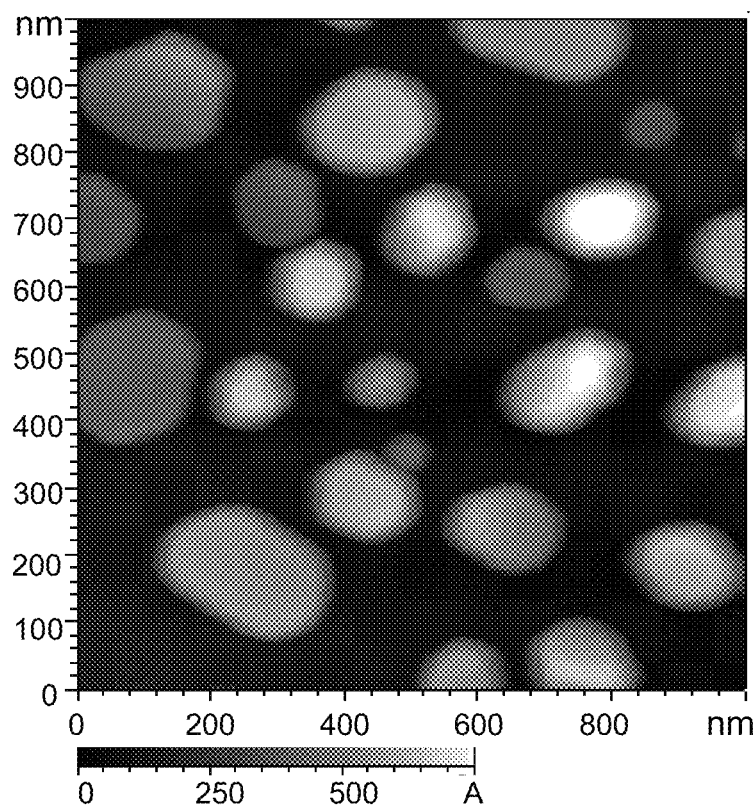
FIGS. 7C and 7E show AFM images of the metal island film on the glass substrates differing by annealing temperature, corresponding to the film before it is brought into contact with non-inert medium.
Figure 7D:
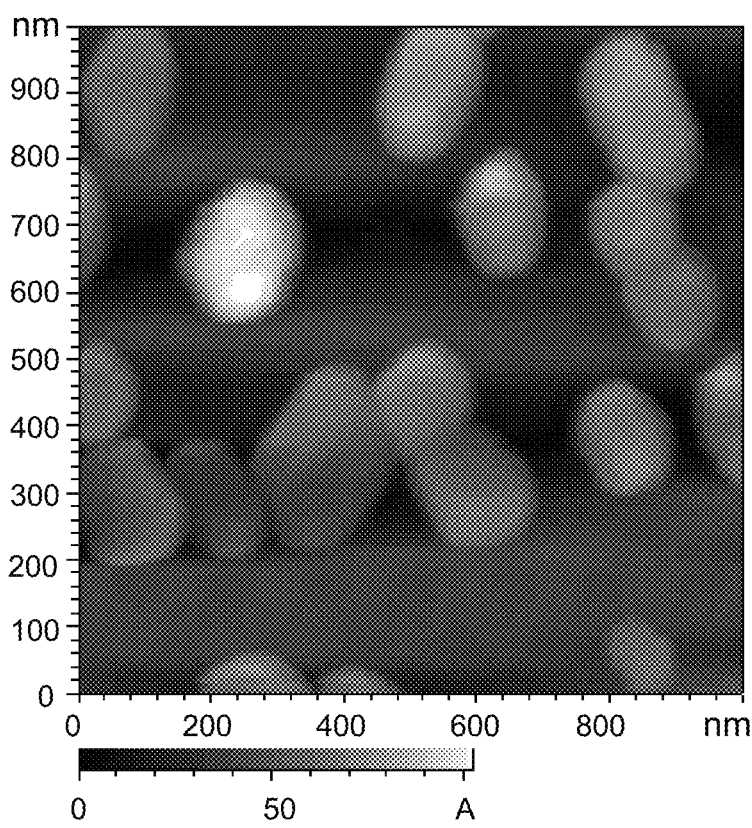
FIGS. 7D and 7F show AFM images of the metal island film on the glass substrates differing by annealing temperature, corresponding to the film after it is brought into contact with non-inert medium.
Figure 7E:
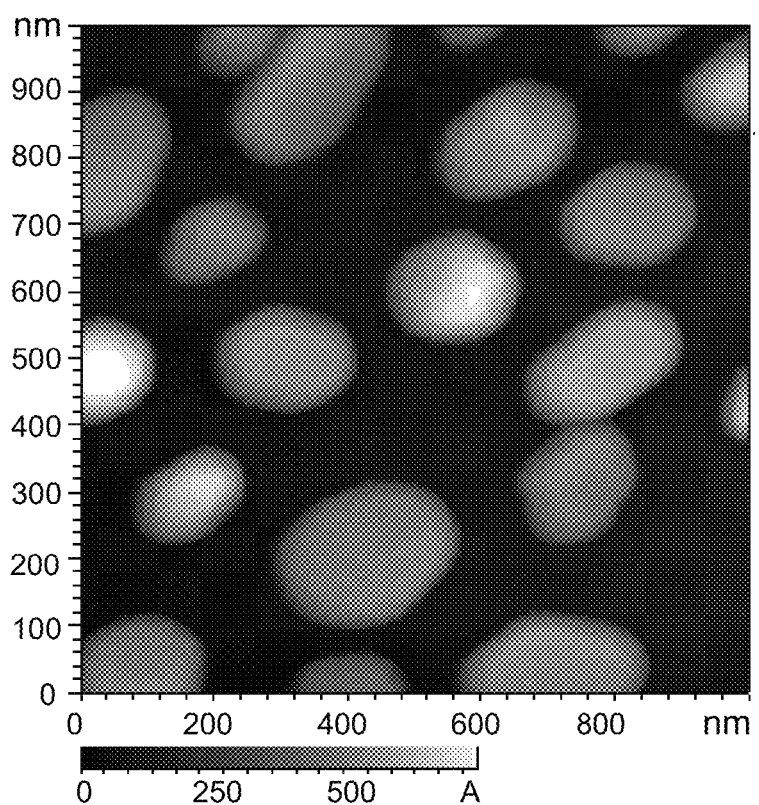
Figure 7F:
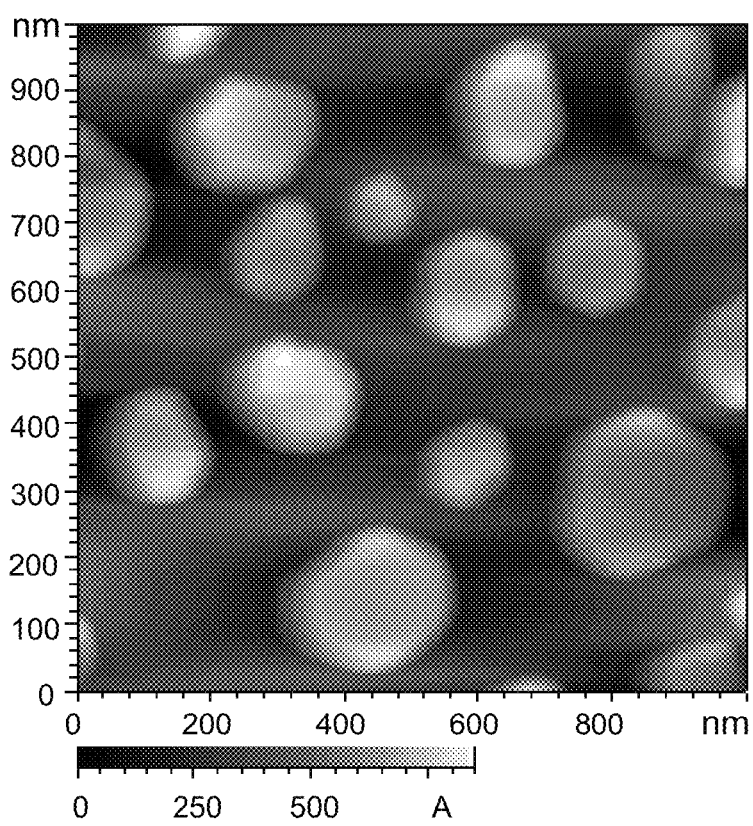

FIGS. 7A and 7B present transmission UV-vis extinction spectra of 10 nm Au island films on cover glass obtained by Au evaporation and annealing for 10 hours at 500° C. (FIG. 7A) and 550° C. (FIG. 7B). Spectra are presented for as-prepared (film deposition by evaporation and annealing at relatively high temperatures close to the transition temperature of the substrate) samples (curves $C_1$), after ethanol wash and dry (curves $C_2$), and then after $C_{18}SH$ self-assembly (curves $C_3$). FIGS. 7C-7E and 7D-7F show AFM images (1×1 micron$^2$ scan) of films corresponding to FIGS. 7A and 7B respectively after ethanol wash and dry (images $I_1$) and after $C_{18}SH$ self-assembly (images $I_2$).

In the case of annealing at 500° C. (i.e., islands are not embedded), a decrease in the extinction is observed after washing in ethanol and drying, while a much more pronounced change in the surface plasmon extinction and the band shape is seen after self-assembly of 1-octadecanethiol ($C_{18}SH$). The AFM images in FIG. 7A show that the Au island film is somewhat unstable toward $C_{18}SH$ self-assembly followed by washing and drying, exhibiting island displacement on the surface. On the other hand, a similar island film annealed at 550° C., just below $T_g$ (i.e., islands are partially embedded), remains essentially intact after the above treatments. Small difference between curve $C_3$ and other curves in FIG. 7B, i.e. the increase in the extinction after $C_{18}SH$ self-assembly, is attributed to change of the refractive index near the island surface due to thiol binding. As explained above, films which are not annealed are unstable and show substantial spectral changes upon treatment with solvents, chemicals and drying.

Figures 8A, 8B:
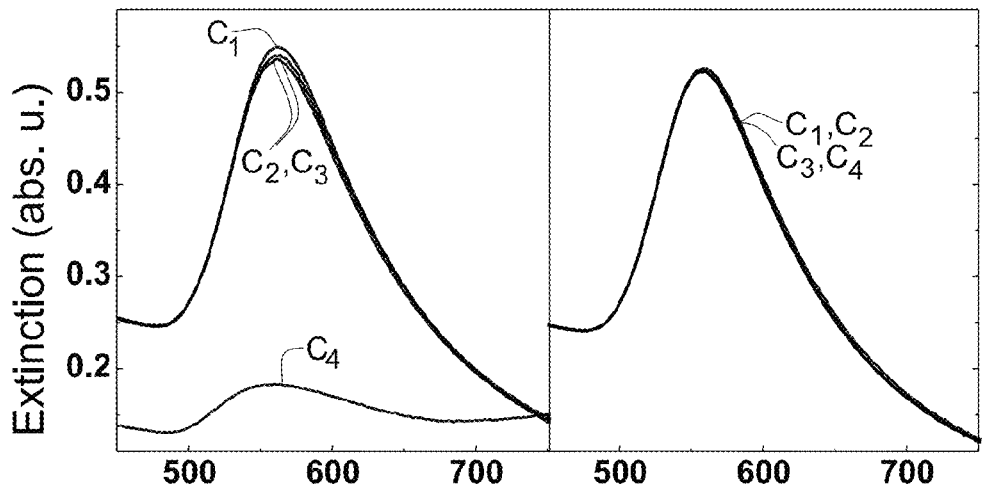
FIGS. 8A-8F show optical responses of Au island films annealed at different temperatures before and after the films are treated with various solvents or solutions.
Figures 8C, 8D:
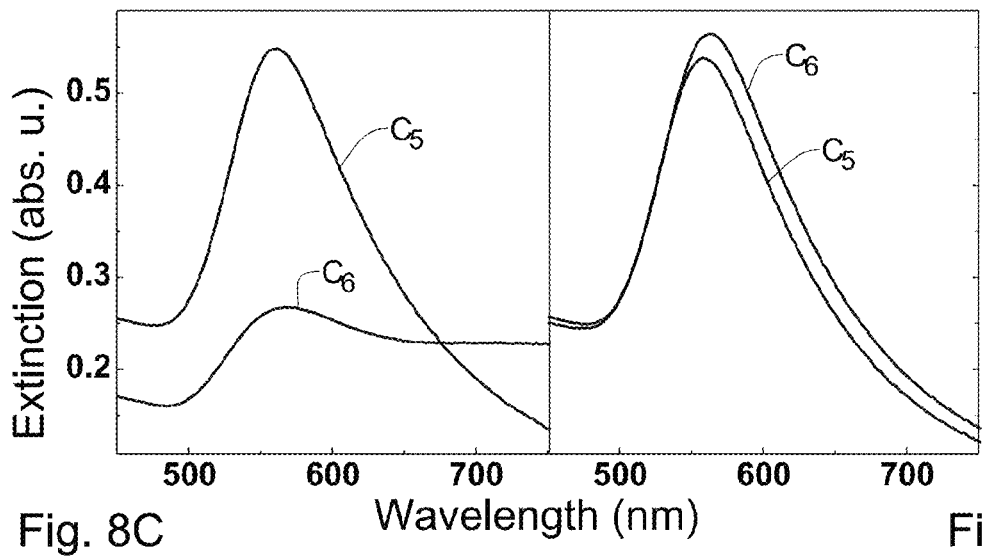
Figures 8E, 8F:
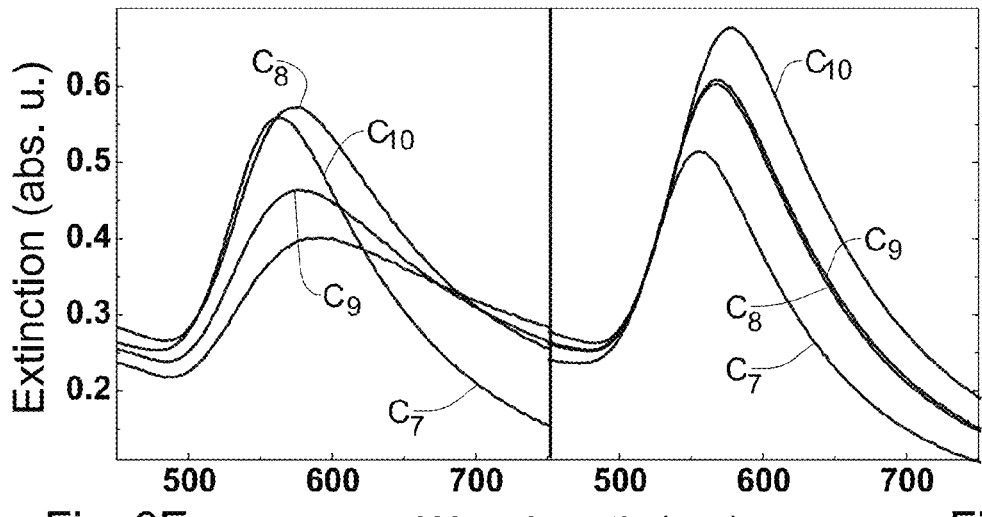

FIGS. 8A-8F present transmission UV-vis spectra of 10 nm Au island films on cover glass annealed at 500° C. (FIGS. 8A, 8C, 8E) and at 550° C. (FIGS. 8B, 8D, 8F). In FIGS. 8A and 8B, curves $C_1$ correspond to initial spectra, while curves $C_2$, $C_3$ correspond to spectra obtained after first and second ethanol wash and dry, and curves $C_4$ correspond to spectra obtained after PBS wash followed by water wash and dry. It is seen that the film annealed at 500° C. (i.e. demonstrating no embedding) shows a small decrease in the extinction after washing in ethanol and drying, while a dramatic change in the SP extinction and the band shape is seen after treatment in PBS solution. As noted above, such samples also fail the adhesive tape test. In marked contrast, a similar island film annealed at 550° C., just below $T_g$, and with embedded islands, remains essentially intact after both treatments, including PBS.

Likewise, as seen from FIGS. 8C and 8D, showing UV-vis spectra of islands after an ethanol wash (curves $C_5$) and after a self-assembly of a monolayer of ss-DNA (curves $C_6$), only Au islands annealed at 550° C. were stable toward such self-assembly. The non-embedded Au island film did not withstand the DNA binding. The difference in extinction between curves $C_5$ and $C_6$ in FIG. 8D is attributed to the change in the local refractive index as a result of DNA adsorption.

Figure 8G:
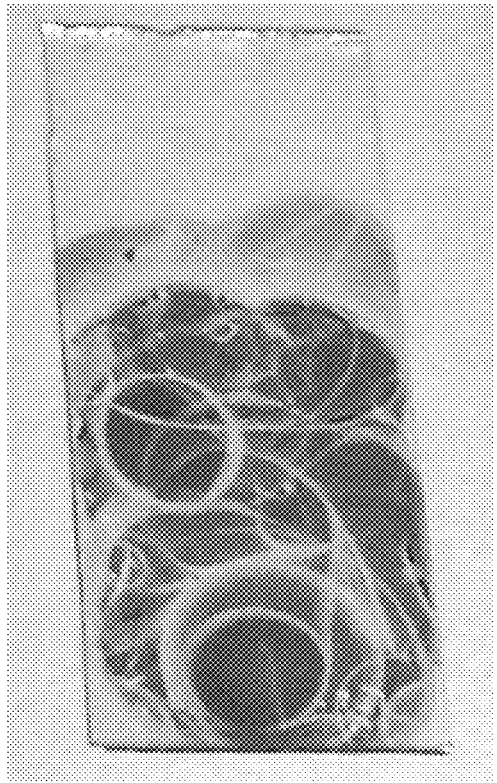
FIGS. 8G and 8H show morphology changing occurring during the sensing sequence of FIGS. 8E and 8F, respectively, showing photographs of 22×9 mm$^2$ slides taken after the treatment sequence, presenting additional evidence that thermally embedded Au island remained stable under the treatments.
Figure 8H:
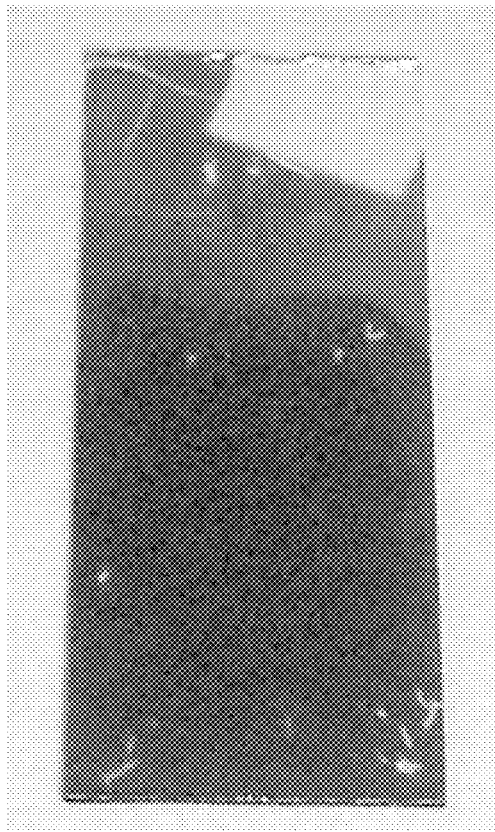

The actual sensing ability of the thermally embedded films is demonstrated using protein-protein, in this example IgG antigen-antibody, recognition. UV-vis spectra $C_7$-$C_{10}$, obtained in a recognition experiment and presented in FIGS. 8E and 8D, are respectively as follows: $C_7$ corresponds to spectra of annealed film after ethanol wash and dry, $C_8$-spectra of these films after IgG antigen adsorption from solution, washing and drying, $C_8$-spectra after exposure to BSA solution, washing and drying, and $C_9$-spectra after antibody-antigen interaction by exposure to IgG antibody solution, washing and drying. The response of the Au film annealed at 500° C. is incomprehensible. This is associated with morphology changing occurring during the sensing sequence. The changes are evident from the respective photograph in FIG. 8G showing the 22×9 mm² slide, taken after the treatment sequence (it should be noted herein that the upper parts of the samples were not treated). In contrast, the Au film annealed at 550° C. was stable and showed high sensitivity to both the IgG antigen binding and the specific antibody-antigen interaction. The photograph in FIG. 8H taken after the treatment sequence presents additional evidence that thermally embedded Au island remained stable under the treatments.

The inventors also conducted an experiment similar to the latter, but in which the bound Rabbit IgG antigen was exposed to Mouse IgG antibody. This treatment caused no change in the SP band, attesting to the specificity and high stability of the system.

Thus, the technique of the present invention shows that metal (e.g. Au) island films evaporated on untreated oxide substrates (glass substrates) and subjected to post-deposition annealing in the presence of oxygen at a temperature T in the vicinity of the substrate glass transition $T_g$ undergo partial embedding in the glass substrate. This embedding is accompanied by formation of a glass rim around the islands. The island films thus obtained often show hexagonal shape or angles with atomically-flat top surfaces characteristic of the (111) crystallographic plane. The films are stable toward immersion in solvents, drying, binding of organic and biological molecules, and pass successfully the adhesive tape test. The adhesion and stability can be obtained without the use of an intermediate adhesion layer or a protective overlayer. The stability of the film optical response and the availability of the simple one-step post-deposition film preparation procedure make these films highly promising for LSPR transducers in sensing applications. Since a stabilizing coating is not used, full sensitivity of the system can be exploited.

Additional details on experiments are presented below.

Gold Island Film Preparation and Dissolution:

Microscope glass cover slides No. 3 (Schott AG borosilicate glass D263T) with $T_g$=557° C. supplied by Menzel-Gläser, and Berliner borosilicate glass (Schott AF45) with $T_g$=662° C., were cut to 22×9 mm² and cleaned by immersion in freshly-prepared hot piranha (1:3 $H_2O_2$:$H_2SO_4$) for 1 h followed by rinsing with triply-distilled water, rinsing in ethanol three times in an ultrasonic bath (Cole-Parmer 8890), and drying under a steam of nitrogen. After cleaning, the slides were mounted in a cryo-HV evaporator (Key High Vacuum) equipped with a Maxtek TM-100 thickness monitor for evaporation of ultrathin Au films. Homogeneous Au deposition was obtained by moderate rotation of the substrate plate. Au (nominal thickness, 10 nm) was resistively evaporated from a tungsten boat at 1-3×10⁻⁶ torr at a deposition rate of 0.005-0.006 nm s⁻¹ (determined by measuring the evaporation time of 0.1 nm Au using a stop-watch). Post-deposition annealing of Au-coated slides was carried out in air (unless otherwise specified) at 500-650° C. for 10 h in an oven (Ney Vulcan 3-550). The heating rate was 5° C. min⁻¹, and the annealed slides were left to cool to room temperature in air. Au films were dissolved from glass substrates by dipping into freshly-prepared aqua regia (1:3 $HNO_3$:HCl) followed by rinsing with triply-distilled water.

Adhesion and Stability Tests:

The strength of the Au island adhesion to glass substrates was evaluated qualitatively using the adhesive tape test: A piece of clear Scotch tape (3M) was pressed against the film and pulled away. Detachment of poorly adhesive films is clearly seen with the naked eye. Stability of the optical response was evaluated by comparing transmission UV-vis spectra before and after the following treatments: stifling in ethanol for 20 min and drying; stirring in PBS solution for 20 min, washing in water and drying under a stream of nitrogen; self-assembly of 1-octadecanthiol ($C_{18}SH$) from 1 mM solution in ethanol for 1 h, followed by washing and drying; self-assembly of a 5' thiol-modified oligonucleotide (ss-DNA, 43 bases) (Integrated DNA Technologies, Inc.) from a 1 µM solution in PBS overnight at room temperature (22-23° C.), followed by washing in PBS and water and drying under a stream of nitrogen.

Sensing of Antigen-Antibody Interaction:

Antigen: A stock solution of 1 mg mL⁻¹ immunoglobulin G (IgG) protein from Rabbit serum (Sigma) was diluted with 0.3 M acetate buffer, pH=4.6 to a final concentration of 100 µg mL⁻¹. Antibody: A stock solution of 1 mg mL⁻¹ Anti-Rabbit IgG antibody produced in goat (Sigma) was diluted with PBS to a final concentration of ~1×10⁻⁶ M. In each step 30 µL of IgG protein were spread on the surface (working area ~1 cm²) and left for 20 min (Rabbit IgG) or 30 min (Anti Rabbit IgG) in air at room temperature (22-23° C.). The slides were then washed in PBS solution for 20 min and in water and dried under a stream of nitrogen. After adsorption of Rabbit IgG the samples were exposed to Bovine Serum Albumine (BSA) (100 µg mL⁻¹) in the same manner as described above to minimize non-specific adsorption of Anti Rabbit IgG.

Measurements:

UV-vis spectroscopy was applied and transmission spectra were obtained with a Varian Cary 50 spectrophotometer using air as the baseline. The wavelength resolution was 1 nm and the average acquisition time per point was 0.1 s. The slide holder was designed to ensure reproducible position of the sample.

Atomic force microscopy (AFM) measurements were carried out in air at room temperature (22-23° C.) using Molecular Imaging (MI) PicoScan™ instrument operating in the acoustic AC mode. The cantilevers used were NSC12 and NSC36 series of ultrasharp silicon (MikroMasch, Estonia) with a resonant frequency of ~150 kHz and an average radius of ≦10 nm.

High-resolution scanning electron microscopy (HRSEM) images were obtained with an Ultra 55 FEG Zeiss high-resolution SEM using the SE detector.

Cross-sectional transmission electron microscopy (cross-sectional TEM) imaging was performed with a Philips CM-120 transmission electron microscope operating at 120 kV, equipped with a CCD camera (2 k×2 k, Gatan Ultrascan 1000). Samples for imaging were embedded in a phenol-based M-Bond 610 epoxy resin (Ted Pella Inc., USA) according to a procedure described previously (M. Wanunu, R. Popovitz-Biro, H. Cohen, A. Vaskevich, I. Rubinstein, *Journal of the American Chemical Society* 2005, 127, 9207).

X-ray diffractometry (XRD) measurements were performed in the θ-2θ Bragg configuration using a rotating anode generator-based TTRAXS III (Rigaku) diffractometer in the parallel beam (PB) mode.

Those skilled in the art will readily appreciate that various modifications and changes can be applied to the embodiments of the invention without departing from its scope defined in and by the appended claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of fabrication of metal islands on an oxide substrate, the method comprising:
   depositing a selected metal on the oxide substrate by evaporation of said selected metal; and
   annealing a film of the selected metal on said substrate at temperatures including an annealing temperature being less than 50° C. lower than a glass transition temperature of said oxide substrate, thereby forming the metal islands depressed into said substrate so that the metal islands become partially embedded within said substrate.

2. The method of claim 1, wherein the annealing temperature substantially does not exceed the transition temperature by more than 100° C.

3. The method of claim 1, wherein said partially embedded islands have generally elongated geometry.

4. The method of claim 1, wherein said partially embedded islands have a generally ellipsoidal-like geometry.

5. The method of claim 1, wherein said substrate is a glass substrate.

6. The method of claim 5, wherein said glass is a borosilicate glass.

7. The method of claim 1, wherein the annealing at said annealing temperature is performed with access of oxygen to said film.

8. The method of claim 1, wherein said metal is gold.

9. The method of claim 1, wherein said annealing is done for a time longer than 30 minutes.

10. The method of claim 1, wherein said annealing is done for a time longer than three hours.

11. The method of claim 1, wherein said film for more than 10% consists of islands of said metal.

12. The method of claim 1, wherein the film of said metal directly interfaces with said substrate without any intermediate adhesive layer between the film and the substrate.

13. The method of claim 1, wherein said annealing temperature is less than 20° C. lower than said transition temperature.

14. The method of claim 1, wherein said annealing provides for stabilization of morphology and optical properties of the metal islands partially embedded in the substrate.

15. The method of claim 14, wherein said annealing provides an increased refractive index sensitivity of the metal islands to foreign materials.

16. A method of fabrication of a metal island film on glass, the method comprising
   depositing a selected metal on the glass by evaporation of said selected metal; and
   annealing a film of the selected metal on glass in presence of oxygen, said annealing being carried out for a selected period of time and at temperatures including an annealing temperature being less than 50° C. lower than a glass transition temperature of said substrate to thereby produce substantially elongated islands partially embedded into said glass.

17. The method of claim 16, wherein a majority of islands with a major axis between 5 and 400 nm is depressed into glass for more than 0.5 nm.

18. The method of claim 16, wherein said annealing provides for stabilization of morphology and optical properties of the metal islands partially embedded in the substrate.

19. The method of claim 18, wherein said annealing provides an increased refractive index sensitivity of the metal islands to foreign materials.

* * * * *